United States Patent [19]

LeClair et al.

[11] 4,411,693

[45] * Oct. 25, 1983

[54] FLOWABLE HERBICIDES

[75] Inventors: Francis J. LeClair, Webster Groves; John M. Surgant, Clayton, both of Mo.

[73] Assignee: Monsanto Company, St. Louis, Mo.

[*] Notice: The portion of the term of this patent subsequent to Feb. 1, 2000, has been disclaimed.

[21] Appl. No.: 247,680

[22] Filed: Mar. 26, 1981

[51] Int. Cl.$^3$ ............... A01N 25/02; A01N 25/00
[52] U.S. Cl. .......................... 71/118; 71/DIG. 1
[58] Field of Search .................... 71/DIG. 1, 118

[56] References Cited

U.S. PATENT DOCUMENTS

| | | | |
|---|---|---|---|
| 2,863,752 | 12/1958 | Hamm et al. | 71/118 |
| 2,891,855 | 6/1959 | Gysin et al. | 71/74 |
| 2,909,420 | 10/1959 | Gysin et al. | 71/74 |
| 3,442,945 | 5/1969 | Olin | 260/562 |
| 3,547,620 | 12/1970 | Olin | 71/118 |
| 3,948,636 | 4/1976 | Marks | 71/112 |

FOREIGN PATENT DOCUMENTS

| | | |
|---|---|---|
| 751164 | 11/1970 | Belgium . |
| 630606 | 11/1961 | Canada . |
| 1421092 | 1/1976 | United Kingdom . |
| 1554595 | 10/1979 | United Kingdom . |

*Primary Examiner*—Catherine L. Mills
*Attorney, Agent, or Firm*—P. A. Coburn; S. M. Tarter; D. W. Peterson

[57] ABSTRACT

The invention relates to a water-based, flowable herbicide composition of 2-chloro-N-isopropylacetanilide herbicide (commonly referred to as propachlor).

7 Claims, No Drawings

FLOWABLE HERBICIDES

BACKGROUND OF THE INVENTION

The invention herein pertains to the field of flowable herbicides. The invention particularly relates to a water-based flowable 2-chloro-N-isopropylacetanilide (commonly referred to as propachlor) herbicide composition.

Commercial formulations of flowable 2-chloro-N-isopropylacetanilide (propachlor) are known in the art; for example, a four pound per gallon propachlor flowable formulation is commercially available under the trade name "Bexton 4L" from the Dow Chemical Co., P.O. Box 1706, Midland, Mich. 48640.

A flowable herbicide formulation may be defined as a physical mixture which contains a finely divided solid or a liquid, suspended in a liquid dispersing medium. A flowable herbicide formulation has advantages over, for example, wettable powder formulation since wettable powder herbicide formulations must be converted into slurries to be used by the farmer in preparing tank mixes for application to the soil. The preparation of slurries of wettable powders of some herbicides, e.g., propachlor, presents certain safety hazards and inconveniences due to the generation of noxious dusts which are irritating to the skin and hazardous to breathe. In addition, wettable powder formulations of propachlor, when prepared as tank mixes, may not disperse well and may also have problems of suspensibility, redispersibility and compatibility with liquid fertilizers.

An emulsifiable concentrate, which is a formulation of the active ingredient dissolved in an organic solvent plus emulsifiers avoids many of the problems of wettable powders, i.e. hazards of noxious dusts, suspensibility and dispersibility problems.

However, water-based flowable herbicide formulations have advantages over emulsifiable concentrates since the latter utilize organic solvents which may be flammable and/or toxic and the cost of which is tied to the cost of oil which continues to escalate.

Additionally, most higher-melting solid herbicides, particularly those with limited solubility in water or organic solvents, have been particularly difficult to formulate in other than wettable powder-type forms. In contrast to emulsifiable concentrates, which rely on ready solubility of the technical active ingredient in a suitable organic solvent such as xylene, chlorobenzene, etc., several herbicides, including propachlor, have low to moderate solubility in any solvent, organic or aqueous and, thus, are not conveniently formulated as emulsifiable concentrates.

Accordingly, it is a particular object of the present invention to provide a water-based, flowable propachlor herbicide composition which may be prepared, transported, stored and used as a one-container herbicide having none of the disadvantages of wettable powder and emulsifiable concentrate formulations.

SUMMARY OF THE INVENTION

This invention relates to a water-based, flowable herbicide containing 2-chloro-N-isopropylacetanilide (propachlor) as the sole active ingredient.

The flowable propachlor formulation of this invention has the following composition by weight:

| Ingredient | % by Weight |
| --- | --- |
| (a) 2-chloro-N—isopropylacetanilide (propachlor) | 38.0–45.0 |
| (b) Hydrated amorphous silicon dioxide | 2.0–6.0 |
| (c) Polyoxypropylene/polyoxyethylene block-copolymer | 2.0–6.0 |
| (d) Taurate surfactant | 0.5–2.0 |
| (e) Hydrated aluminum silicate | 0.5–2.0 |
| (f) Flocculent | 0.5–1.0 |
| (g) Inert, low-freezing point solvent | 5.0–10.0 |
| (h) Silicon defoamer | 0.5–2.0 |
| (i) Water | balance | the solid components of said composition having a particle size of no greater than 25 microns.

In the water-based, flowable herbicide composition disclosed herein, the active ingredient, propachlor, is present in a preferred concentration of from 40.0–44.0% by weight of the total composition, preferably at 42.0% by weight of total composition. In general, the composition will contain from 3.8 to 4.3 pounds of active ingredient per U.S. gallon of total composition.

The active ingredient, i.e. propachlor, in the water-based, flowable herbicide formulation is maintained in a dispersion/suspension system comprising a unique and critical combination of (1) hydrated amorphous silica, (2) aqueous and/or alcoholic solution of polyoxypropylene/polyoxyethylene block copolymer, (3) taurate surfactant and (4) hydrated aluminum silica. It is critical to employ these components in certained prescribed ratios both in relation to each other and to the concentration of the propachlor herbicide component in order to obtain formulations with the desired storage stability and water dispersibility.

As used herein, the term "hydrated amorphous silica" refers to a finely-divided silica such as naturally occurring Kieselguhr or an artificial silica. Artificial silica is silica which has been produced by a chemical reaction as compared with naturally occurring silica such as Kieselguhr. Preferred for use herein are artificial silicas as, for example, artificial silicas sold under the tradename "Hi-Sil 233" (manufactured by PPG Industries, Inc., Pittsburgh, PA 15222) and "Zeofree 80" (manufactured by J. M. Huber Corp., Edison, N.J. 08817). There is suitably used at from 2.0–6.0% by weight of the total composition, preferably 4.0% by weight, of silica in the form of water-free or hydrated silica gel or other amorphous silica.

The term "polyoxypropylene/polyoxyethylene block co-polymer" refers to a product which may be formed by reacting propylene glycol first with propylene oxide and then with ethylene oxide. It is preferred to use a product having polyoxypropylated propylene glycol backbone of molecular weight 3,000 to 3,500 and containing 50% of ethylene oxide units so that the total molecular weight is 6,000 to 7,000. Examples of such block co-polymers are "Pluraflo E4", "Pluraflo E5" and "Pluronic P105", tradenames of nonionic polyoxypropylene/polyoxyethylene block co-polymer surfactants sold by BASF Wyandotte Corp., Industrial Chemicals Group, Wyandotte, Mich., 48192. The block co-polymer is present in the composition at from 2.0–6.0% by weight, preferably 2.75–3.0% by weight of total composition.

As used herein, the term "taurate surfactant" refers to anionic surfactants such as sodium N-cyclohexyl-N-palmitoyl taurate, sodium N-methyl-N-oleoyl taurate, respectively sold under the tradenames, Igepon CN-42, Igepon T-33, T-43, T-51, T-73, T-77 and T-74 by GAF Corp., Chemical Products, 140 W. 51st St., New York, N.Y. 10020. Sodium N-methyl-N-oleoyl taurate is also available under the tradename "Adinol" from Croda Chemicals, Ltd., England. Preferred for use herein is sodium N-methyl-N-oleoyltaurate. The anionic surfactant is present in the formulation of the present invention at from 0.5%-2.0% by weight of the composition, preferably at 1.0% by weight.

The term "hydrated aluminum silica" as used herein refers to such materials as barden clay or kaolin, which are low surface area materials which have an electrostatic surface charge and thus are able to enhance the stability of the dispersion. These materials are commercially available from many sources as will be readily recognized by those skilled in the art. The "hydrated aluminum silica" component of the formulation described herein is present at from 0.5%-2.0% by weight, preferably at 1.0% by weight of the total composition.

As used herein, the term "flocculent" refers to a suitable salt, i.e., one which contains a polyvalent cation and which is soluble in the amount of water present in the composition which acts to cause the solids in the composition to form small, loosely aggregated bits or particles suspended in the liquid in the composition. Suitable salts which may be mentioned are $CaCl_2$, $MgCl_2$, $CaBr_2$, $Mg(C_2H_3O_2)_2$, $MgBr_2$, $MnBr_2$ and the like, preferred for use herein is $CaCl_2$. The flocculent is present in the composition at from 0.5%-1.0% by weight, preferably at 0.75% by weight of total composition.

Lower alkylene glycols, e.g. ethylene or propylene glycol, are examples of suitable freeze-point depressants useful in the invention described herein. Amounts of these components ranging from 5.0%-10.0% by weight of total composition will adequately provide the composition with the desired antifreeze protection. Preferably, about 8.0% by weight of total composition is used in the formulation of the present invention.

The term "silicon defoamer" as used herein refers to silicon antifoaming agents exemplified by the following silicon antifoaming agents commercially available under the tradenames "Antifoam F1", manufactured by Hodag Chemical Corp., 7247 Central Park Avenue, Skokie, Ill. 60076; "Mazu DF 1005", available from Mazer Chemicals, Inc., 3938 Porett Dr., Gurnee, Ill. 60031; "Corak 100", sold by Coral Chemical Co., and "Sag 47", sold by Union Carbide Corp., 270 Park Avenue, New York, N.Y. 10017. From 0.05-0.20% by weight of the defoaming agent has been found to be useful in the present invention, preferably about 0.1% by weight of total composition is used herein.

The novel water-based, flowable propachlor herbicide composition of this invention is prepared according to the following process. In general the process of this invention involves mixing the relevant components in appropriate quantities in a pre-grind operation in order to blend the ingredients and obtain a suitable solids particle size distribution and facilitate the final wet grinding operation.

While the order of addition of the components is not critical, it has been found that the following order of addition of the components of the water-based, propachlor formulation facilitates the homogeneity of the formulation and also the grinding process. To the mixing vessel is charged the following components in the order indicated: water, flocculent, block copolymer, anti-freeze agent, taurate surfactant, antifoam agent, amorphous silicon dioxide, barden clay and finally, propachlor.

A preferred particle size distribution of the solids in the pre-grind operation is as follows: 95% less than 100 microns; 75% less than 80.0 microns; 50% less than 60 microns; and 25% less than 30 microns.

The final grinding operation may be conducted in vertical or horizontal media mills by using stainless steel, ceramic or other ball grinding materials which are inert with respect to the reaction components. Critical parameters in the final wet-grind operation are that the temperature be maintained below about 20° C. and the grinding or milling operation continued until the solids particle size distribution is as follows: 95% less than 20.0 microns; 75% less than 15.0 microns; 50% less than 10.0 microns and 25% less than 5.0 microns. In preferred flowable herbicide embodiments, the solids particle-size distribution is as follows: 95% less than 2.0 microns; 75% less than 10.0 microns, 50% less than 5.0 microns and 25% less than 2.5 microns.

EXAMPLE 1

This example describes a preferred embodiment of the invention for preparing a water based, flowable herbicide containing propachlor as the active ingredient.

The following components were fed to a mixer for a pre-grind mixing blend operation in the indicated proportions:

| Component | % by Weight | lb/Gal | Lb/2000 Gal |
|---|---|---|---|
| [a]Propachlor (95%) | 45.26 | 4.300 | 8600 |
| Hi-Sil 233 ® | 4.00 | 0.380 | 760 |
| Barden Clay (kaolin) | 1.00 | 0.095 | 190 |
| Pluronic 105 ® | 2.81 | 0.267 | 534 |
| Igepon T77 ® | 1.00 | 0.095 | 190 |
| $CaCl_2$ | 1.00 | 0.095 | 190 |
| Ethylene glycol | 8.01 | 0.761 | 1521 |
| Silicon Defoamer (Corak 100 ®) | 0.05 | 0.005 | 10 |
| Water | 36.87 | 3.502 | 7005 |
|  | 100.0 | 9.500 | 19,000 |

[a]4.3 Lbs/Gal, 94% propachlor is equivalent to 4.04 Lbs/Gal of 100% material.

The above formulation was ground in one gallon increments for 10 minutes for each gallon while maintaining the temperature at less than about 25° C., preferably about 20° C., until the solids were reduced to a particle size corresponding to the following distribution; 95% less than 48 microns; 75% less than 35.5 microns; 50% less than 23 microns and 25% less than 13 microns. The mixture was sampled for assay; any necessary adjustments were made based on the sample analysis.

The pre-ground mixture was then pumped to a surge tank, and fed to a horizontal media mill, e.g., a Dyno-Mill, at a throughput volume of 4-8 liters/hour, while maintaining the temperature at about 18°-20° C. Solids in the formulation leaving the media mill had a particle size distribution as follows: 95% less 20.0 microns; 75% less than 10.0 microns; 50% less than 5.0 microns and 25% less than 2.5 microns.

Similar flowable formulations as the above having varying amounts of active ingredients have also been prepared in vertical media mills, called attritors. In any case, the essential criteria are that the process cooling temperatures be maintained at or below about 20° C., formulation assay be maintained at the correct composition and that the solids particle size be maintained below about 48–50 microns in the pre-mix and below 25 microns, preferably below 20 microns and still more preferably below 5 microns, i.e., according to the size distribution shown in Example 1.

The water-based, propachlor flowable compositions of this invention can be used as a preemergence herbicide to selectively control weeds in crops, particularly corn, sorghum and soybeans. The compositions can be applied at rates of 4 to 6 pounds per acre. The exact rate to be used will depend upon the crop, the soil type, the climate and the weeds to be controlled. The treatment will control grasses and certain broadleaved weeds. The exact rate to be used can be readily selected by one skilled in the art from the available literature.

The following Example is presented to further illustrate this invention.

EXAMPLE 2

Corn, sorghum, yellow foxtail and barnyardgrass were planted in triplicate in 4 inch pots and the treatments listed in the attached table were applied preemergence using a belt sprayer. Both treatments received ¼ inch overhead irrigation immediately following application of the herbicide treatment. Visual estimates of percent inhibition were made approximately 12 days after treatment and the results recorded. The observations are summarized in Table I.

TABLE I

| TREAT-MENT | LB/A | % INHIBITION | | | |
|---|---|---|---|---|---|
| | | CORN | SORGHUM | BARNYARD GRASS | YELLOW FOXTAIL |
| Composition of Ex. 1 | 1/32 | 0 | 0 | 0 | 43.3 |
| | 1/16 | 0 | 0 | 10.0 | 51.7 |
| | ⅛ | 0 | 0 | 23.3 | 75.0 |
| | ¼ | 0 | 0 | 55.0 | 83.3 |
| | ½ | 0 | 0 | 76.7 | 82.7 |
| | 1 | 0 | 1.7 | 91.7 | 98.3 |
| | 2 | 0 | 5.0 | 99.3 | 100.0 |
| | 4 | 3.3 | 1.7 | 100.0 | 100.0 |
| *65 WP | 1/32 | 0 | 0 | 1.7 | 5.0 |
| | 1/16 | 0 | 0 | 3.3 | 18.3 |
| | ⅛ | 0 | 0 | 5.0 | 30.0 |
| | ¼ | 0 | 0 | 53.3 | 68.3 |
| | ½ | 0 | 0 | 78.3 | 91.7 |
| | 1 | 0 | 5.0 | 93.3 | 96.0 |
| | 2 | 0 | 0 | 93.3 | 98.7 |
| | 4 | 0 | 0 | 97.0 | 100.0 |

*Ramrod ® 65 - wettable powder formulation of 2-chloro-N—isopropylacetanilide (propachlor) herbicide manufactured by Monsanto Company, St. Louis, Missouri 63166.

As shown in Table I, the water-based, flowable propachlor herbicide of the present invention controls the weeds, barnyard grass and yellow foxtail comparable to the control achieved by a commercially-available wettable powder formulation of propachlor herbicide.

As indicated above the primary benefits of the water-based flowable propachlor herbicide composition of this invention relate to the elimination of the use of organic solvents, noxious fumes and dusts, improved suspensibility and redispersability, while maintaining crop safety and efficacy comparable to analogous herbicide formulations of the prior art. In addition, the flowable herbicides herein provide the convenience and economy of a one-container formulation; i.e., there is no necessity to buy, transport, store, measure and mix the components of two or more containers.

Although this invention has been described with respect to specific modifications, the details thereof are not to be construed as limitations, since it will be apparent that various equivalents and modifications may be resorted to without departing from the spirit and scope of the invention.

We claim:

1. A water-based, flowable herbicide composition which comprises by weight:
   (a) 38.0% to 45.0% 2-chloro-N-isopropylacetanilide herbicide;
   (b) 2.0% to 6.0% of a hydrated amorphous silicon dioxide;
   (c) 2.0% to 6.0% of a polyoxypropylene/polyoxyethylene block-copolymer;
   (d) 0.5% to 2.0% of a taurate surfactant;
   (e) 0.5% to 2.0% of a hydrated aluminum silicate;
   (f) 0.5% to 1.0% of a flocculent;
   (g) 5.0% to 10.0% of an anti-freeze agent;
   (h) 0.5% to 2.0% of a silicon antifoaming agent; and
   (i) balance being water;
   the solid components of said composition having a particle size of no greater than 25 microns.

2. A composition according to claim 1 which comprises by weight:
   (a) 40.0% to 44.0% 2-chloro-N-isopropylacetanilide herbicide;
   (b) 3.0% to 5.0% of a hydrated amorphous silicon dioxide;
   (c) 2.75% to 3.0% of a polyoxypropylene/polyoxyethylene block-copolymer;
   (d) 0.75% to 1.5% of a taurate surfactant;
   (e) 0.75% to 1.5% of a hydrated aluminum silicate;
   (f) 0.5% to 1.0% of a flocculent;
   (g) 6.0% to 8.0% of an anti-freeze agent;
   (h) 0.75% to 1.5% of a silicon antifoaming agent; and
   (i) balance being water;
   the solid components of said composition having a particle size of no greater than 25 microns.

3. A composition according to claim 1 wherein said taurate surfactant is sodium N-methyl-N-oleoyltaurate.

4. A composition according to claim 1 wherein said hydrated aluminum silicate is barden clay or kaolin.

5. A composition according to claim 1 wherein said flocculent is CaCl$_2$.

6. A composition according to claim 1 wherein said antifreeze agent is ethylene glycol.

7. A composition according to claim 1 which comprises by weight:
   (a) 42.0% of 2-chloro-N-isopropylacetanilide herbicide;
   (b) 4.0% hydrated, amorphous silicon dioxide;
   (c) 3.0% polyoxypropylene/polyoxyethylene block co-polymer;
   (d) 1.0% of sodium N-methyl-N-oleoyltaurate;
   (e) 1.0% hydrated aluminum silicate;
   (f) 0.75% CaCl$_2$ flocculent;
   (g) 8.0% ethylene glycol;
   (h) 0.1% silicon antifoaming agent; and
   (i) balance being water;
   the solid components of said composition having a particle size of no greater than 25 microns.

* * * * *